US011672838B2

(12) United States Patent
Kim

(10) Patent No.: US 11,672,838 B2
(45) Date of Patent: Jun. 13, 2023

(54) **COMPOSITION FOR PREVENTION OR TREATMENT OF NEUROLOGICAL OR MENTAL DISORDERS COMPRISING EXTRACELLULAR VESICLES DERIVED FROM *LACTOBACILLUS PARACASEI***

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

(*) Notice: Subject to any disclaimer, the term of this patent is extended or adjusted under 35 U.S.C. 154(b) by 0 days.

(21) Appl. No.: 17/343,901

(22) Filed: Jun. 10, 2021

(65) Prior Publication Data
US 2021/0386800 A1  Dec. 16, 2021

Related U.S. Application Data

(63) Continuation of application No. PCT/KR2021/003075, filed on Mar. 12, 2021.

(30) Foreign Application Priority Data

Jun. 16, 2020 (KR) .......... 10-2020-0072685
Dec. 7, 2020 (KR) .......... 10-2020-0169167

(51) Int. Cl.
*A61K 35/747* (2015.01)
*A61P 25/00* (2006.01)

(52) U.S. Cl.
CPC ............ *A61K 35/747* (2013.01); *A61P 25/00* (2018.01)

(58) Field of Classification Search
CPC .................................................. A61K 35/747
See application file for complete search history.

(56) References Cited

U.S. PATENT DOCUMENTS

| 10,617,727 | B2* | 4/2020 | Lue ............. A61K 35/747 |
| 10,987,386 | B2* | 4/2021 | Kim ............. A61P 29/00 |
| 2013/0243728 | A9* | 9/2013 | McDonagh ........ C07K 14/4703 435/254.22 |
| 2017/0239302 | A1* | 8/2017 | Lue ............. A61K 38/482 |
| 2019/0209628 | A1* | 7/2019 | Kim ............. A61K 35/747 |
| 2019/0343902 | A1* | 11/2019 | Lue ............. A61K 35/747 |
| 2020/0040242 | A1* | 2/2020 | Fukushima .......... C10M 105/48 |
| 2020/0206282 | A1* | 7/2020 | Kim ............. A61K 9/007 |
| 2020/0306327 | A1* | 10/2020 | Stenman ............. A61P 1/00 |
| 2020/0330531 | A1* | 10/2020 | Stenman ............. A61P 25/24 |
| 2021/0030821 | A1* | 2/2021 | Kim ............. A61K 35/747 |
| 2021/0085731 | A1* | 3/2021 | Tsai ............. A61P 1/00 |
| 2021/0228668 | A1* | 7/2021 | May ............. A61K 36/28 |
| 2021/0379127 | A1* | 12/2021 | Biffi ............. A61K 35/747 |
| 2021/0386800 | A1* | 12/2021 | Kim ............. A61P 25/00 |

FOREIGN PATENT DOCUMENTS

| EP | 3 351 616 A1 | 7/2018 | |
| KR | 10-2018-0019482 A | 2/2018 | |
| KR | 10-2098067 B1 | 4/2020 | |
| KR | 2257130 B1 * | 5/2021 | ........... A23L 33/135 |
| WO | 2017/047962 A1 | 3/2017 | |
| WO | 2019/119261 A1 | 6/2019 | |
| WO | 2019/121666 A1 | 6/2019 | |
| WO | WO-2021061789 A1 * | 4/2021 | |
| WO | WO-2021108195 A1 * | 6/2021 | ........... A61K 35/741 |
| WO | WO-2021256665 A1 * | 12/2021 | ........... A23L 33/135 |
| WO | WO-2021256793 A1 * | 12/2021 | |

OTHER PUBLICATIONS

Khandestan et al, J. Gorgan University of Medical Sciences, Autumn 2020, 22/3:65-72. abstract only (Year: 2020).*
Mulak et al, World Journal of Gastroenterology. Oct. 7, 2015, 21/37:10609-10620 (Year: 2015).*
Umbrello et al, Journal Transl Medicine, 2016, 14:298. 11 pages. (Year: 2016).*
https://my.clevelandclinic.org/health/diseases/15345-paralysis?view=print; accessed Sep. 22, 2022 (Year: 2022).*
Dawson et al., Nat Neurosci., 2018; 21(10):1370-1379 (Year: 2018).*
NIH, https://www.nia.nih.gov/news/new-genetically-modified-mouse-model-mimics-multiple-aspects-human-alzheimers-disease; Jul. 29, 2021 (Year: 2021).*
Huang el al., "Lactobacillus paracasei PS23 Delays Progression of Age-Related Cognitive Decline in Senescence Accelerated Mouse Prone 8 (SAMP8) Mice", Nutrients, 2018, vol. 10, pp. 894 (13 pages).
Choi et al., "Lactobacillus paracasei-derived extracellular vesicles attenuate the intestinal inflammatory response by augmenting the endoplasmic reticulum stress pathway", Experimental & Molecular Medicine, (2020), 15 pages.
Extended European Search Report for corresponding European Patent Application No. 21732162.9, dated Sep. 30, 2022, 8 pages.

* cited by examiner

*Primary Examiner* — Brian Gangle
*Assistant Examiner* — Lakia J Jackson-Tongue
(74) *Attorney, Agent, or Firm* — Vorys, Sater, Seymour and Pease LLP; Mih Suhn Koh

(57) ABSTRACT

Provided are a method for preventing, improving, or treating a neurological disorder, mental disorder, senescence, or symptoms thereof, comprising administering to a subject in need thereof vesicles derived from *Lactobacillus paracasei* as an active ingredient, and a pharmaceutical or functional food composition comprising the vesicles.

8 Claims, 16 Drawing Sheets

Thioflavin-S staining

EXP2 (post-stress day 28-30)

TST

COMPOSITION FOR PREVENTION OR TREATMENT OF NEUROLOGICAL OR MENTAL DISORDERS COMPRISING EXTRACELLULAR VESICLES DERIVED FROM *LACTOBACILLUS PARACASEI*

CROSS-REFERENCE TO RELATED APPLICATIONS

This application is a Continuation of PCT/KR2021/003075 filed Mar. 12, 2021, which claims the benefit of priority from Korean Patent Application No. 10-2020-0072685 filed Jun. 16, 2020 and Korean Patent Application No. 10-2020-0169167 Dec. 7, 2020, the contents of each of which are incorporated herein by reference in its entirety.

TECHNICAL FIELD

The present invention relates to a composition for preventing, improving, or treating a neurological disorder or mental disorder, comprising extracellular vesicles derived from *Lactobacillus paracasei* as an active ingredient, and the like.

This application claims priority to and the benefit of Korean Patent Application Nos. 10-2020-0072685 and 10-2020-0169167 filed in the Korean Intellectual Property Office on Jun. 16, 2020 and Dec. 7, 2020, respectively, and all the contents disclosed in the specification and drawings of the applications are incorporated in this application.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and human lifespan. In particular, degenerative brain diseases such as dementia, Parkinson's disease, autism spectrum disorder, and Lou Gehrig's disease, mental disorder such as stress disorder, and depression, and the like as intractable chronic diseases in the aging society of the 21st century have become a major problem for the health of the people as main diseases that determine the human lifespan and quality of life.

Degeneration of nerve cells (neurons) leads to abnormalities in the structure and function of brain-nerve tissues due to the death of nerve cells. Many neurodegenerative diseases such as amyotrophic lateral sclerosis (Lou Gehrig's disease), Parkinson's disease, Alzheimer's disease, fatal familial insomnia, and Huntington's disease occur as a result of the neurodegenerative process. Further, diseases such as Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), and mitochondrial recessive ataxia syndrome are also caused by degenerative changes in nerve cells. Such diseases are untreatable, and thus lead to progressive degeneration and/or death of nerve cells.

As studies on the mechanism of pathogenesis of these diseases progress, many similarities were found to relate such diseases at the subcellular level. Finding such similarities gives hope for the development of treatments that can simultaneously improve many diseases. The fact that abnormal proteins are produced and the resulting induced apoptosis play an important role in the development of various degenerative neurological disorders has been revealed. Brain tissues of a patient with a degenerative neurological disorder increase autophagy by accumulating autophagosomes, which plays an important role in eliminating the misfolded proteins occurring abnormally during the development process of the degenerative neurological disorder. Recently, in studies on the pathogenesis of cellular senescence, the fact has been revealed that cellular senescence is caused by various stresses, and in particular, AMPK signals activated by metabolic stress prevent cellular senescence by increasing autophagy.

It is known that the accumulation of mitochondrial DNA (mtDNA) mutations and the overproduction of reactive oxygen species (ROS) promote neuronal cell senescence. Appropriate production of reactive oxygen species suppresses cellular senescence by continuously activating the AMPK signals, but the overproduction of excessive reactive oxygen species causes abnormalities in mitochondrial functions, thereby leading to cell death. Diseases such as Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), and mitochondrial recessive ataxia syndrome are likely caused by mutations in mitochondrial DNA by reactive oxygen species produced in mitochondria, resulting in mitochondrial dysfunction and cellular senescence to cause degenerative nerve diseases.

Meanwhile, depression is an illness in which the function of the brain that regulates emotions is altered and negative emotions appear, and is a disease that affects 300 million or more people worldwide. Depression is associated with chemical imbalances in neurotransmitters such as dopamine, serotonin, and norepinephrine. Among them, serotonin is a neurotransmitter found in cerebrospinal fluid, and circulates in the brain and functions as a neurotransmitter. Serotonin is closely related to emotional expression, and deficient serotonin may cause emotional instability, which leads to an increase in anxiety and concern, and impulsive tendencies appear. Therefore, among pharmaceuticals currently used as therapeutic agents for depression, there are many pharmaceuticals which act to suppress the re-absorption of serotonin so that serotonin stays in the brain for a long time.

Recently, it has been revealed that mental disorders such as depression, autism, and schizophrenia are closely associated with abdominal pain. Abdominal pain is accompanied by diarrhea and constipation, and leads to irritable bowel syndrome when repeated, which has been shown to be associated with gut microbial dysbiosis. It has been reported that when an intestinal bacterial imbalance occurs due to bad food, antibiotic use, and the like, harmful intestinal microorganisms cause cracks in the healthy large intestine defense membrane, causing intestinal leakage, and then toxins derived from harmful bacteria are absorbed systemically, causing or exacerbating depression [Pharmacotherapy. 2015 October; 35(10): 910-6].

It is known that the number of microorganisms that coexist in the human body reaches 100 trillion, which is about 10-fold larger than that of human cells, and the number of genes of microorganisms is 100-fold larger than that of humans. A microbiota or microbiome refers to a microbial community including bacteria, archaea and eukarya present in a given habitat.

Bacteria that coexist in our bodies and bacteria that exist in the surrounding environment secrete nanometer-sized vesicles to exchange information such as genes, low molecular compounds, and proteins with other cells. The mucosa forms a physical defense membrane through which particles having a size of 200 nanometers (nm) or more cannot pass, so that bacteria coexisting in the mucosa cannot pass through the mucosa, but bacteria-derived extracellular vesicles have a size of approximately 20 to 200 nanometers, and thus relatively freely pass through epithelial cells via the mucosa to be absorbed in our bodies. Locally secreted bacterial-derived extracellular vesicles are absorbed through the epithelial cells of the mucosa to induce a local inflammatory response, and vesicles that have passed through the epithelial cells are systemically absorbed to be distributed to respective organs, and regulate immune and inflammatory responses in the distributed organs. For example, extracellular vesicles derived from pathogenic Gram-negative bacteria such as *Escherichia coli* locally cause an inflammatory response and cancer, and promotes a systemic inflammatory response and blood coagulation through a vascular endothelial cell inflammatory response when absorbed into blood vessels. In addition, such vesicles are absorbed into muscle cells on which insulin acts, and the like to cause insulin resistance and diabetes. In contrast, extracellular vesicles derived from beneficial bacteria may be absorbed into specific cells of respective organs to suppress the outbreak of a disease by regulating core immune functions and metabolic dysfunctions.

*Lactobacillus paracasei* is a Gram-positive bacillus, and grows well not only in anaerobic environments but also in aerobic environments and is known as a beneficial bacterium that coexists in our bodies. Bacteria secrete extracellular vesicles (EVs) having a bilayer structure into the extracellular environment for the exchange of intercellular proteins, lipids, genes, and the like. Extracellular vesicles derived from gram-positive bacteria such as *Lactobacillus paracasei* include peptidoglycan and lipoteichoic acid, which are constituents of bacterial cell walls, in addition to bacteria-derived proteins and nucleic acids.

However, there is no case where vesicles secreted by *Lactobacillus paracasei* have been used for the prevention or treatment of a neurological disorder or mental disorder.

DISCLOSURE

Technical Problem

As a result of intensive studies to solve the above-mentioned problems in the related art, the present inventors confirmed that when vesicles were isolated from *Lactobacillus paracasei* and orally administered, the vesicles were delivered to the brain, and when the vesicles were orally administered to an animal model of degenerative brain disease, improvement in cognitive functions such as memory and learning ability was shown, the formation of an amyloid plaque, which is an abnormal protein, was suppressed, and the above efficacy was caused by a mechanism through which such efficacy increases the proliferation of nerve cells and the formation of nerve cell dendrites. Furthermore, in order to evaluate whether vesicles derived from *Lactobacillus paracasei* were efficacious for a mental disorder due to mental stress, the present inventors observed that anti-stress and antidepressant effects on mental disorder were shown at almost the same level as an antidepressant imipramine in the case of administering vesicles derived from *Lactobacillus paracasei* to an animal model of mental disorder due to mental stress, thereby completing the present invention based on this.

Thus, an object of the present invention is to provide a pharmaceutical composition for preventing or treating a neurological disorder or mental disorder, comprising vesicles derived from *Lactobacillus paracasei* as an active ingredient.

In addition, another object of the present invention is to provide a food composition for preventing or improving a neurological disorder or mental disorder, comprising vesicles derived from *Lactobacillus paracasei* as an active ingredient.

In addition, still another object of the present invention is to provide an inhalable composition for preventing or treating a neurological disorder or mental disorder, comprising vesicles derived from *Lactobacillus paracasei* as an active ingredient.

Furthermore, yet another object of the present invention is to provide a pharmaceutical composition for preventing or treating senescence, comprising vesicles derived from *Lactobacillus paracasei* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a pharmaceutical composition for preventing or treating a neurological disorder or mental disorder, comprising vesicles derived from *Lactobacillus paracasei* as an active ingredient.

In addition, the present invention provides a food composition for preventing or improving a neurological disorder or mental disorder, comprising vesicles derived from *Lactobacillus paracasei* as an active ingredient.

In addition, the present invention provides an inhalable composition for preventing or treating a neurological disorder or mental disorder, comprising vesicles derived from *Lactobacillus paracasei* as an active ingredient.

In addition, the present invention provides a pharmaceutical composition for preventing or treating senescence, comprising vesicles derived from *Lactobacillus paracasei* as an active ingredient.

As an exemplary embodiment of the present invention, the neurological disorder may be one or more disorders selected from the group consisting of mild cognitive impairment, dementia, Alzheimer's disease, Parkinson's disease, Huntington's disease, amyotrophic lateral sclerosis (ALS), Batten disease, Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), and mitochondrial recessive ataxia syndrome, but is not limited thereto.

As another exemplary embodiment of the present invention, the mental disorder may be one or more disorders selected from the group consisting of anxiety disorders, post-traumatic stress disorder (PTSD), panic disorder, depression, autism spectrum disorder, attention deficit/hyperactivity disorder (ADHD), and schizophrenia, but is not limited thereto.

As still another exemplary embodiment of the present invention, the vesicles may have an average diameter of 10 to 1000 nm, but the average diameter is not limited thereto.

As yet another exemplary embodiment of the present invention, the vesicles may be isolated from a *Lactobacillus paracasei* culture solution, but are not limited thereto.

As yet another exemplary embodiment of the present invention, the vesicles may be obtained using vesicles isolated from a food prepared by adding *Lactobacillus paracasei*, but are not limited thereto.

As yet another exemplary embodiment of the present invention, the vesicles may be naturally or artificially secreted from *Lactobacillus paracasei*, but are not limited thereto.

As yet another exemplary embodiment of the present invention, the senescence may be brain or neuronal senescence, but is not limited thereto.

Further, the present invention provides a method for preventing or treating a neurological disorder or mental disorder, the method comprising administering the composition to an individual.

In addition, the present invention provides a use of vesicles derived from *Lactobacillus paracasei* for preventing or treating a neurological disorder or mental disorder.

Furthermore, the present invention provides a use of vesicles derived from *Lactobacillus paracasei* for preparing a drug for preventing or treating a neurological disorder or mental disorder.

Further, the present invention provides a method for preventing, treating, or improving senescence, the method comprising administering a composition comprising vesicles derived from *Lactobacillus paracasei* as an active ingredient to an individual.

In addition, the present invention provides a use of a composition comprising vesicles derived from *Lactobacillus paracasei* as an active ingredient for preventing, treating, or improving senescence.

Furthermore, the present invention provides a use of vesicles derived from *Lactobacillus paracasei* for preparing a drug for preventing or treating senescence.

Advantageous Effects

The present inventors confirmed that vesicles derived from *Lactobacillus paracasei* were delivered to the brain when orally administered, and confirmed that when vesicles derived from *Lactobacillus paracasei* were orally administered to a disease model of a degenerative neurological disorder, learning ability and memory were improved to normal levels, the deposition of amyloid plaques in brain tissues was suppressed, the proliferation of stem cells in the hippocampus was improved to normal levels, and the formation of nerve cell dendrites was restored to normal levels. Thus, the present invention is expected to be able to be used as a composition for preventing, improving, or treating a neurological disorder or mental disorder, comprising vesicles derived from *Lactobacillus paracasei* as an active ingredient.

Further, the present inventors confirmed that when vesicles derived from *Lactobacillus paracasei* was administered to an animal model of mental disorder, there was an effect of effectively suppressing the occurrence of mental dysfunction due to stress, so that the vesicles derived from *Lactobacillus paracasei* according to the present invention can also be usefully used for the development of a pharmaceutical or health functional food for preventing a mental disorder, improving symptoms thereof, or treating the mental disorder.

MODES OF THE INVENTION

Figure 1:
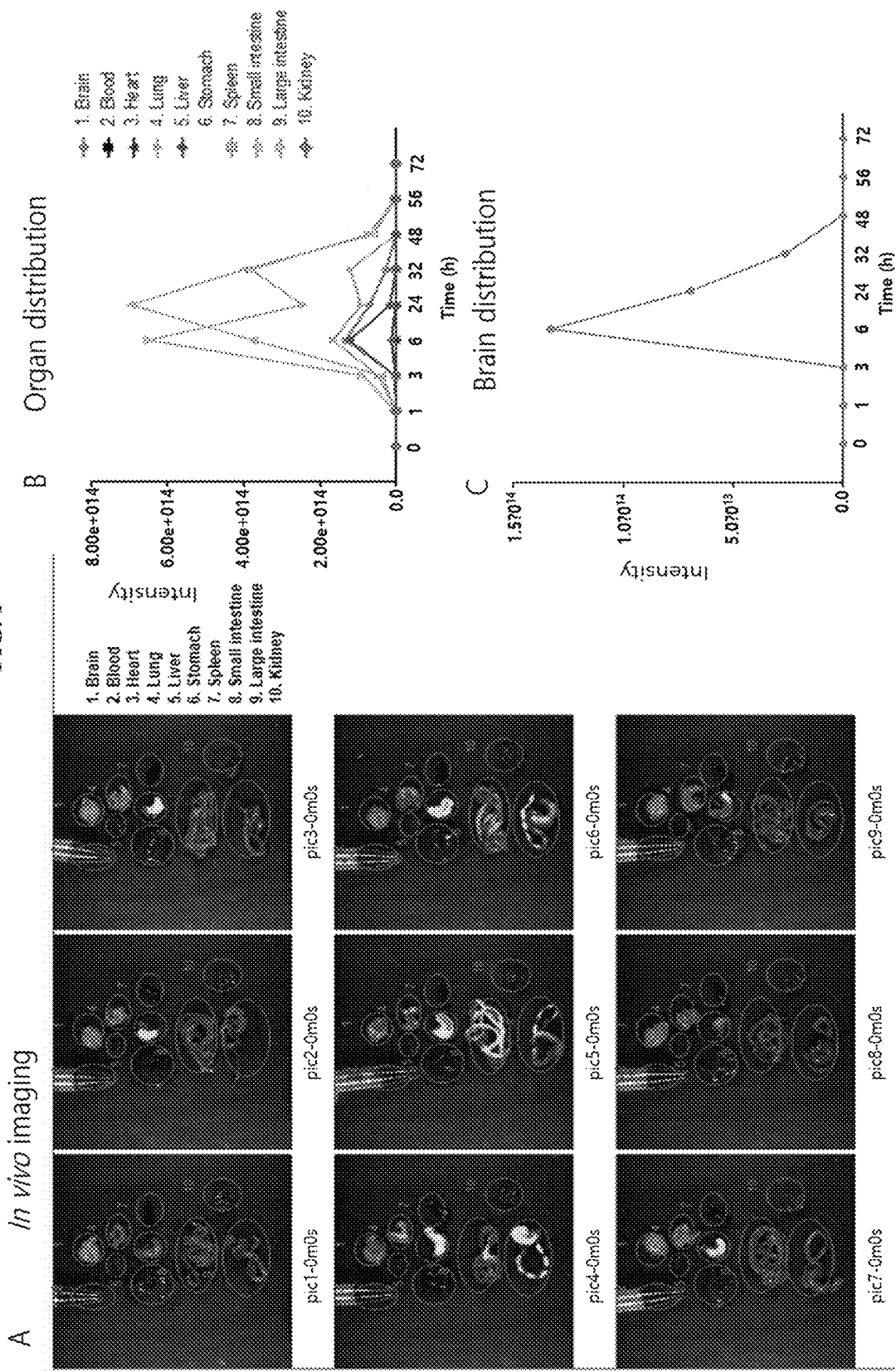
FIG. 1 illustrates a set of photos of the distribution patterns of vesicles derived from *Lactobacillus paracasei*, which is a Gram-positive bacterium, taken over time after the vesicles are orally administered to mice (A), the results of showing the distribution patterns of *Lactobacillus paracasei*-derived vesicles by organ by removing various organs over time after oral administration in a graph (B), and the results of showing the fluorescence intensity of *Lactobacillus paracasei*-derived vesicles distributed in the brain over time in a graph (C).

The present invention relates to vesicles derived from *Lactobacillus paracasei* bacteria and a use thereof.

Hereinafter, the present invention will be described in detail.

The present inventors confirmed that when vesicles derived from Gram-negative bacteria having lipopolysaccharide (LPS) in the outer cell membrane are orally administered, the vesicles are not distributed in the brain, but when vesicles derived from *Lactobacillus paracasei*, which is a Gram-positive bacterium, are orally administered, the vesicles were delivered to the brain. Further, when *Lactobacillus paracasei*-derived vesicles were orally administered to APP and PS1 transgenic mice with a brain disease, the learning ability and memory of the transgenic mice were improved to normal levels, and the deposition of amyloid plaques in brain tissues was suppressed. In addition, it was confirmed that the proliferation of stem cells in the hippocampus was improved to normal levels and the formation of nerve cell dendrites was restored to normal levels. Furthermore, as a result of intensive studies to investigate the correlation between *Lactobacillus paracasei*-derived vesicles and a mental disorder, the present inventors observed that administration of *Lactobacillus paracasei*-derived vesicles to an animal model of mental disorder induced by mental stress exhibited effects on mental dysfunctions such as an emotional disorder, thereby completing the present invention based on this.

Thus, the present invention provides a composition for preventing, improving, or treating a neurological disorder or mental disorder, comprising vesicles derived from *Lactobacillus paracasei* as an active ingredient.

The composition includes a pharmaceutical composition, a food composition, and an inhalable composition.

As used herein, the term "neurological disorder" refers to a disorder caused by damage and senescence of nerve cells resulting from abnormalities in mitochondrial function due to various stresses, and includes mild cognitive impairment, dementia, Alzheimer's disease, Parkinson's disease, Huntington's disease, amyotrophic lateral sclerosis (ALS), Batten disease, Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), mitochondrial recessive ataxia syndrome, and the like, but is not limited thereto.

As used herein, the term "mental disorder" refers to a pathological mental state that affects human thoughts, emotions, behaviors, and the like, and collectively refers to a state in which mental function is impaired. In the present invention, the mental disorder includes anxiety disorders, post-traumatic stress disorder (PTSD), panic disorder, depression, autism spectrum disorder, attention deficit/hyperactivity disorder (ADHD), schizophrenia, and the like.

As used herein, the term vesicle or extracellular vesicle refers to a structure formed of a nano-sized membrane secreted from various bacteria, and in the present invention, the term collectively refers to all structures formed of a membrane naturally secreted from *Lactobacillus paracasei*, or artificially produced. The vesicles may be isolated from a culture solution including *Lactobacillus paracasei* bacterial cells by using one or more methods selected from the group consisting of heat treatment, centrifugation, ultra-high speed centrifugation, high pressure treatment, extrusion, sonication, cell lysis, homogenization, freezing-thawing, electroporation, mechanical decomposition, chemical treatment, filtration by filter, gel filtration chromatography, free-flow electrophoresis, and capillary electrophoresis. Further, a process such as washing for removing impurities and concentration of obtained vesicles may be further included.

The vesicles of the present invention may be isolated from a *Lactobacillus paracasei* culture solution or a food prepared by adding *Lactobacillus paracasei*, and the vesicles may be naturally or artificially secreted from *Lactobacillus paracasei*, but are not limited thereto.

The method for isolating vesicles from the culture solution or fermented food of the *Lactobacillus paracasei* of the present invention is not particularly limited as long as the vesicles are included. For example, vesicles may be isolated using a method such as centrifugation, ultra-high speed centrifugation, filtration by a filter, gel filtration chromatography, free-flow electrophoresis, or capillary electrophoresis, and a combination thereof, and further, a process such as washing to remove impurities and concentration of obtained vesicles may be further included.

In the present invention, vesicles isolated by the method may have an average diameter 10 to 1000 nm, 10 to 900 nm, 10 to 800 nm, 10 to 700 nm, 10 to 600 nm, 10 to 500 nm, 10 to 400 nm, 10 to 300 nm, 10 to 200 nm, 10 to 100 nm, 10 to 90 nm, 10 to 80 nm, 10 to 70 nm, 10 to 60 nm, 10 to 50 nm, 10 to 40 nm, or 20 to 40 nm, but the average diameter is not limited thereto.

The amount of the vesicles in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC) 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC) 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan (propylene glycol monostearate), glycerin, Adeps solidus, buytyrum Tego-G, cebes Pharma 16, hexalide base 95, cotomar, Hydrokote SP, S-70-XXA, S-70-XX75(S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to an individual via various routes. All administration methods can be predicted, and the pharmaceutical composition may be administered via, for example, oral administration, subcutaneous injection, intraperitoneal administration, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases. Specifically, the effective amount of the composition according to the present invention may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, gender, body weight, age, and the like, the dosage is not intended to limit the scope of the present invention in any way.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

In addition, the present invention provides a food composition for preventing or improving a neurological disorder or mental disorder, comprising vesicles derived from *Lactobacillus paracasei* as an active ingredient.

The food composition may be a health functional food composition, but is not limited thereto.

The vesicles according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

Further, the present invention may be provided in the form of an inhalable composition comprising *Lactobacillus paracasei*-derived vesicles as an active ingredient.

In the case of a preparation for inhalation, the compound may be formulated according to a method known in the art, and may be conveniently delivered in the form of an aerosol spray from a pressurized pack or a nebulizer by using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a metered amount. For example, a gelatin capsule and a cartridge for use in an inhaler or insufflator may be formulated so as to contain a powder mixture of a compound and a suitable powder base such as lactose or starch.

Further, the present invention provides a composition for preventing or treating senescence or senescence-related diseases comprising vesicles derived from *Lactobacillus paracasei* as an active ingredient.

In the present invention, senescence collectively refers to all physiological changes in the body that occur over time, and refers to a biological phenomenon that occurs variously due to a number of factors depending on an individual. When looking specifically at the senescence phenomenon, functional changes in each constituent organ and tissue occur, and the senescence of an individual is ultimately caused by the senescence of the cells that make up the individual.

In the present invention, the senescence may be brain or neuronal senescence, but is not limited thereto.

Hereinafter, preferred Examples for helping the understanding of the present invention will be suggested. However, the following Examples are provided only to more easily understand the present invention, and the contents of the present invention are not limited by the following Examples.

EXAMPLES

Example 1: Isolation of Vesicles Derived from *Lactobacillus paracasei*

In order to isolate an extracellular vesicle (EV) derived from *Lactobacillus paracasei*, *Lactobacillus paracasei* was inoculated into a de Man-Rogosa and Sharpe (MRS) medium, cultured at 37° C. and 200 rpm until absorbance ($OD_{600\ nm}$) was 1.0 to 1.5, and then *Lactobacillus paracasei* was re-inoculated into a Luria Bertani (LB) medium and cultured. Then, a supernatant from which bacterial cells had been removed was obtained by recovering the culture solution including bacterial cells and performing centrifugation at 4° C. and 10,000 g for 20 minutes. The obtained supernatant was again filtered using a 0.22 μm filter, and the filtered supernatant was concentrated to a volume of 50 mL or less using a 100 kDa Pellicon 2 Cassette filter membrane (Merck Millipore) and a MasterFlex pump system (Cole-Parmer). A vesicle derived from *Lactobacillus paracasei* (MDH-001) was isolated by filtering the concentrated supernatant again using a 0.22 µm filter. In the following examples, experiments were performed using the isolated vesicle.

Example 2. Evaluation of Pharmacokinetic Characteristics of Vesicles Derived from *Lactobacillus paracasei* Bacteria In order to investigate the pharmacokinetic characteristics of *Lactobacillus paracasei*-derived vesicles during oral administration, the fluorescence expressed in the body and each organ from immediately before administration to 72 hours after administration was measured by orally administering vesicles stained with a fluorescent staining reagent to mice.

As illustrated in A and B of FIG. 1, it was confirmed that the fluorescently stained *Lactobacillus paracasei*-derived vesicles gradually spread in the body over time. When each organ was separately observed, a fluorescent signal of *Lactobacillus paracasei*-derived vesicles was observed in the stomach 1 hour after oral administration, and fluorescent signals were observed in the small intestine, large intestine, and lungs from 3 hours. Further, it was confirmed that the fluorescent signals of the stomach, small intestine, large intestine, and lungs were maintained for up to 56 hours.

In addition, as illustrated in C of FIG. 1, a fluorescent signal was specifically observed in the brain from 3 hours after administration, and this signal was detected up to 48 hours.

In order to investigate whether the pharmacokinetic characteristics of *Lactobacillus paracasei*-derived vesicles are strain-specific or Gram-negative bacteria-specific phenomena, the fluorescence expressed by the same method was measured by orally administering, to mice, *Acinetobacter baumannii*-derived vesicles, which are Gram-negative bacteria-derived vesicles, stained with a fluorescent staining reagent.

Figure 2:
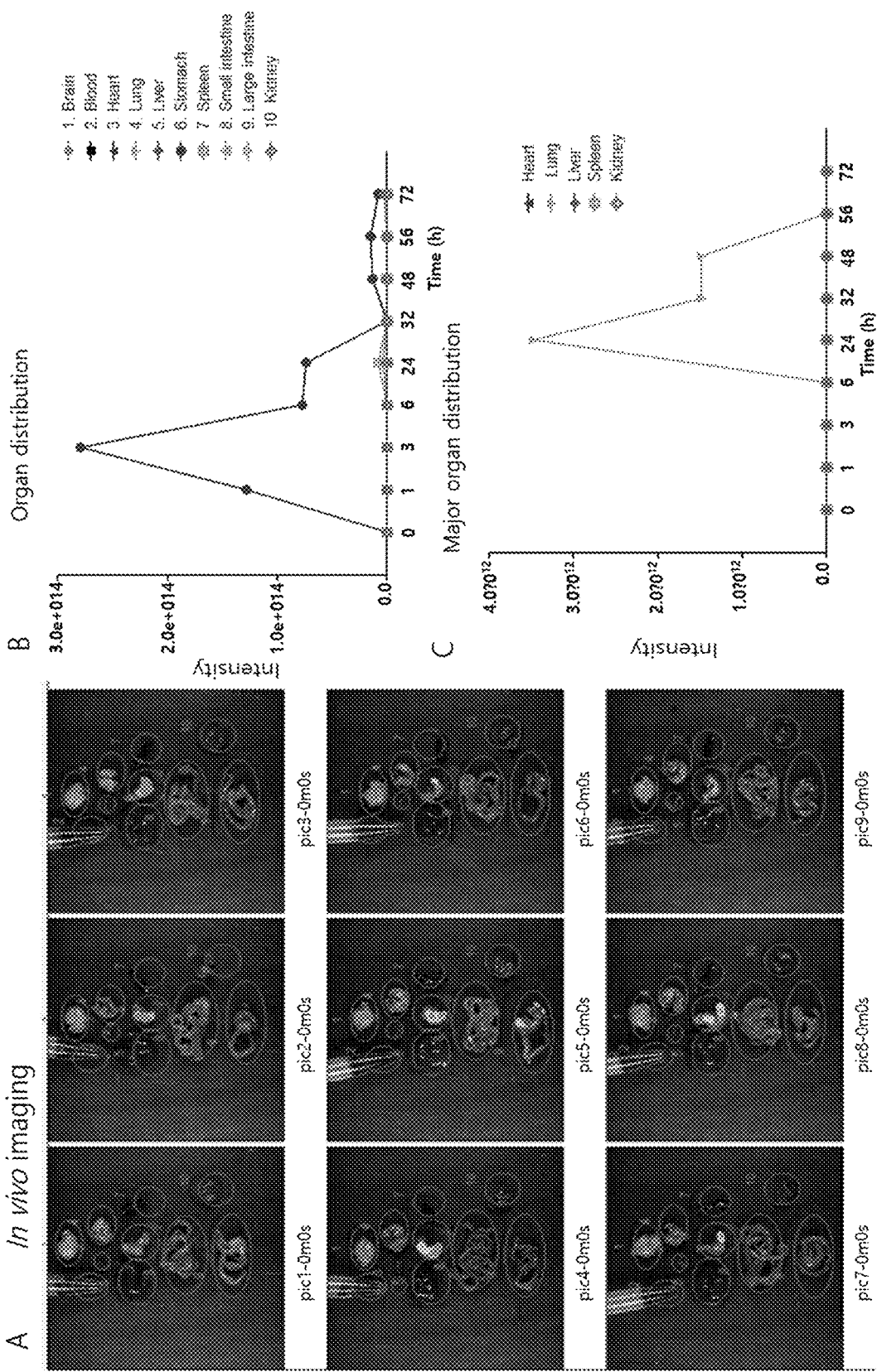
FIG. 2 illustrates a set of photos of the distribution patterns of vesicles derived from *Acinetobacter baumannii*, which is a Gram-negative bacterium, taken over time after the vesicles are orally administered to mice (A), the results of showing the distribution patterns of *Acinetobacter baumannii*-derived vesicles by organ by removing various organs over time after oral administration in a graph (B), and the results of showing the fluorescence intensity of *Acinetobacter baumannii*-derived vesicles distributed in major organs over time in a graph (C).

As illustrated in A of FIG. 2, it was confirmed that the strongest fluorescent signal was observed in the stomach 3 hours after oral administration of *Acinetobacter baumannii*-derived vesicles, and the fluorescent signal confirmed in the stomach decreased over time.

Furthermore, as illustrated in B and C of FIG. 2, in the case of *Acinetobacter baumannii*-derived vesicles, no fluorescent signal was measured in the brain. Through the results, it was confirmed that the pharmacokinetic characteristics of *Lactobacillus paracasei*-derived vesicles were strain-specific phenomena.

Figure 3:
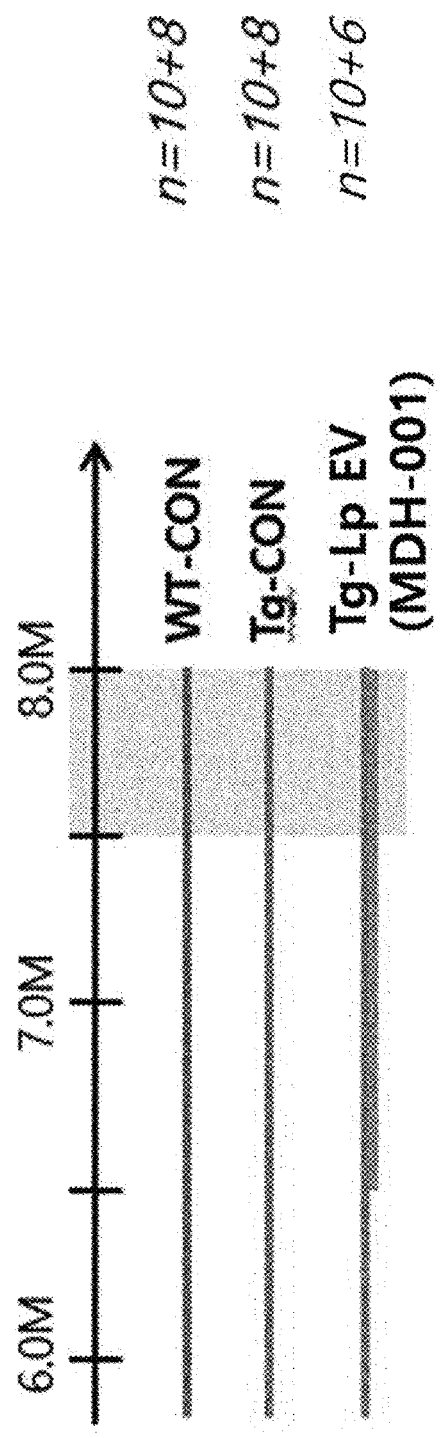
FIG. 3 is a view illustrating the administration period and a schematic diagram of an animal experimental design using a degenerative brain disease mouse model. WT-CON refers to a normal mouse group, Tg-CON refers to a degenerative brain disease mouse model group, and Tg-LP EVs refers to a group in which *Lactobacillus paracasei*-derived extracellular vesicles (MDH-001) were orally administered to a degenerative brain disease mouse model.

Example 3. Evaluation of Efficacy for Cognitive Function of *Lactobacillus paracasei*-Derived Vesicles in Mouse Model of Neurological Disorder A Tg-APP/PS1 mouse is a representative degenerative brain disease mouse model, which is an animal model which shows the deposition of histologically detectable plaques from 6.5 months and in which cognitive dysfunction is stably detected at the age of 7 to 8 months. Behavioral and histological examinations were performed using the present mouse model after dividing the mice into a normal mouse group (WT-CON), a degenerative brain disease mouse model group (Tg-CON), and a group (Tg-Lp EV, MDH-001) in which *Lactobacillus paracasei*-derived vesicles were orally administered to a degenerative brain disease mouse model at a dose of 50 µg/mouse as in FIG. 3.

Figure 4:
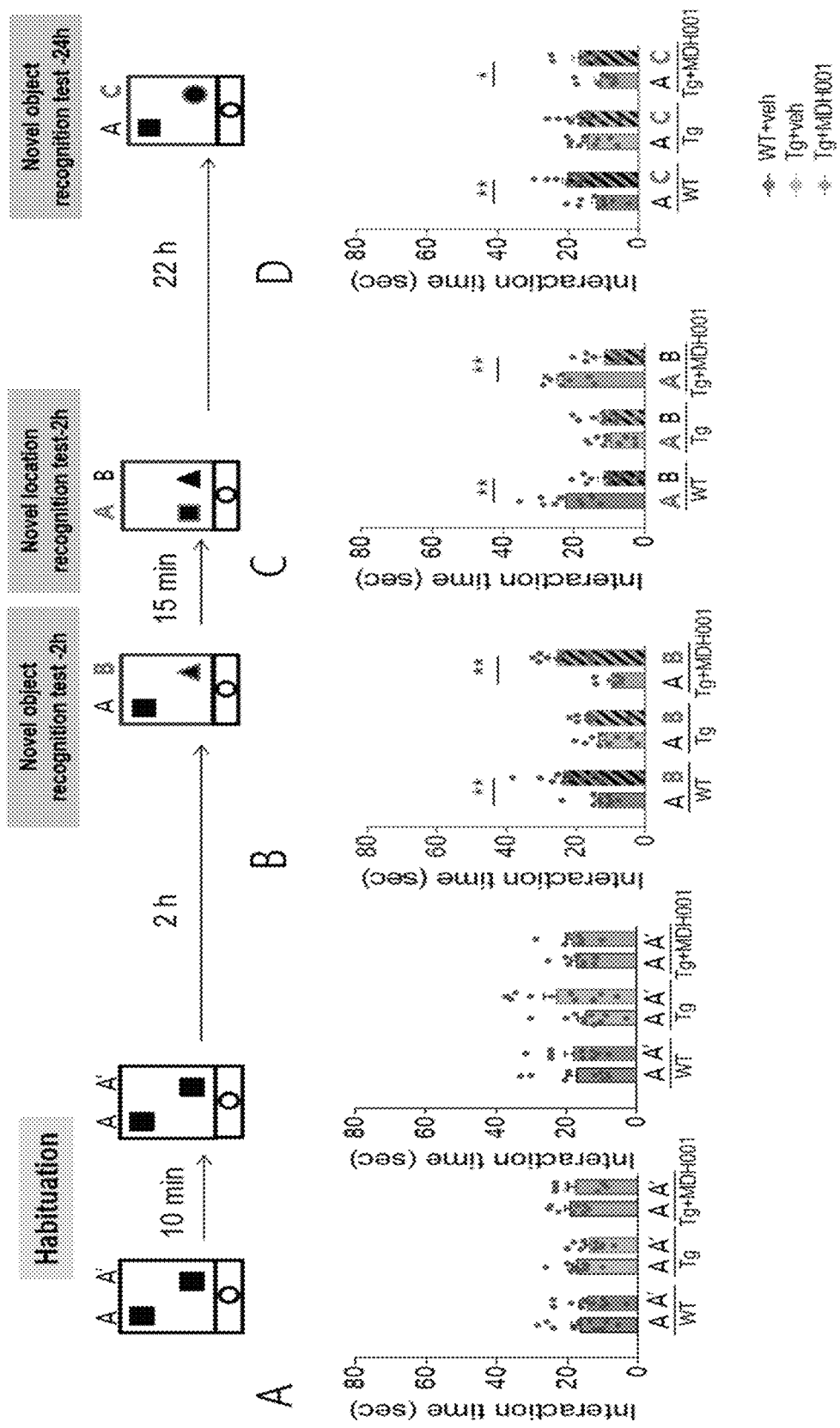
FIG. 4 illustrates the results of performing tests on the ability to recognize objects and positions in a normal mouse group (WT-CON), a degenerative brain disease mouse model (Tg-CON) group, and a group (Tg+MDH001) to which *Lactobacillus paracasei*-derived vesicles (MDH-001) were orally administered and then comparing the test results, which are a result (A) showing the time it takes for mice to find two objects, a result (B) showing the time it takes for mice find a new object after 2 hours, a result (C) showing the time it takes for mice to find an object whose position has been changed after 15 minutes, and a result (D) showing the time it takes for mice to find a new object after 24 hours.

In order to evaluate cognitive function by administration of *Lactobacillus paracasei*-derived vesicles in a degenerative brain disease mouse model, the time it took for the mice to find an object during a period of 10 minutes was measured by exposing each group of WT-CON, Tg-CON, and Tg+MDH-001 to a new object or an object whose position was changed, as illustrated in FIG. 4.

As a result, as illustrated in B and D of FIG. 4, it was confirmed that in a novel object recognition test (NOR) measured after 2 or 24 hours, the time to find a new object was longer in WT-CON and Tg+MDH-001, but there was no change in Tg-CON.

As illustrated in C of FIG. 4, it was confirmed that even in a novel location recognition test (NLR), the time to find an object whose position has been moved was longer in WT-CON and Tg+MDH-001, but there was no change in Tg-CON. The results mean that *Lactobacillus paracasei*-derived vesicles suppress the progression of short-term and long-term cognitive impairments in mice with a degenerative brain disease.

Example 4. Evaluation of Efficacy for Learning Ability of *Lactobacillus paracasei*-Derived Vesicles in Mouse Model of Neurological Disorder In order to evaluate the learning ability efficacy by administration of *Lactobacillus paracasei*-derived vesicles in a degenerative brain disease mouse model based on the above examples, as illustrated in FIG. 5, an evaluation in which a hidden platform is searched for after training mice to search for the hidden platform in a water bottle for 5 days was performed.

Figure 5:
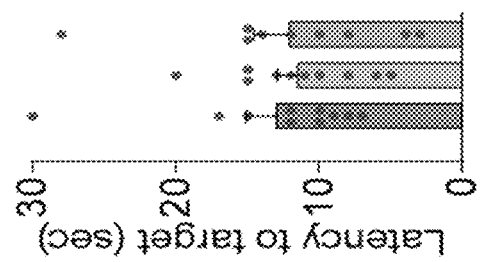
FIG. 5 illustrates the results of evaluating the learning ability efficacies in a normal mouse group (WT-CON), a degenerative brain disease mouse model (Tg-CON) group, and a group (Tg+MDH001) to which *Lactobacillus paracasei*-derived vesicles (MDH-001) were orally administered, which are a result (A) showing the time it takes for mice in the three groups to find a hidden platform during a learning period of 5 days, a result (B) showing the time the mice spend in each part of a water bottle during the learning ability test, and a result (C) showing the time it takes for the mice in each group to find a visible platform.
Figure 5:
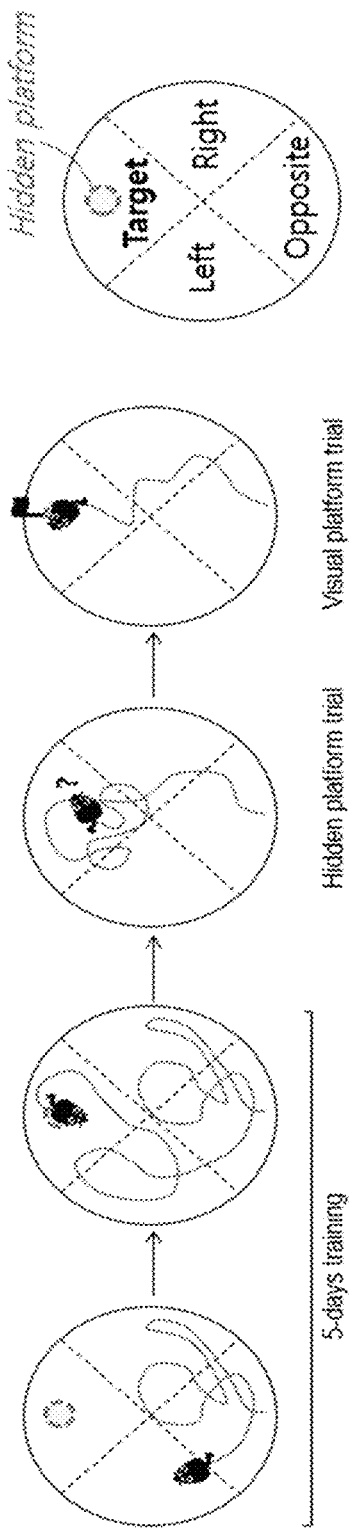
Figure 5:
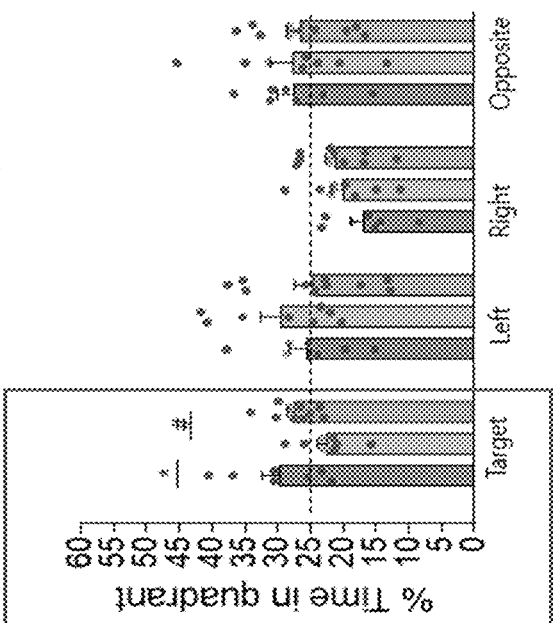
Figure 5:
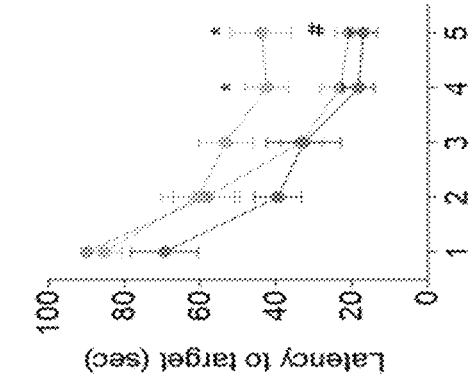

As a result, as illustrated in A of FIG. 5, a normal mouse group (WT-CON) had the fastest time to find the hidden platform during the training period of 5 days, a group (Tg+MDH-001) in which *Lactobacillus paracasei*-derived vesicles were orally administered to a degenerative brain disease mouse model also showed a learning time similar to that of the WT-CON group, but a degenerative brain disease mouse model group (Tg-CON), which is a positive control, showed the slowest learning time.

As illustrated in B of FIG. 5, it was confirmed that the WT-CON group stayed at the platform position for a long time even during the time when looking for and staying at the position of the hidden platform, and the Tg+MDH-001 group also showed a time similar to that of the WT-CON group, but the Tg-CON group spent the shortest time at the platform position while walking around in places excluding the platform. Through the results, it was confirmed that the *Lactobacillus paracasei*-derived vesicles had a spatial perceptual learning restoration effect and a spatial perceptual memory restoration effect in mice with a degenerative brain disease.

Example 5. Evaluation of Efficacy for Memory Ability of *Lactobacillus paracasei*-Derived Vesicles in Mouse Model of Neurological Disorder In order to re-evaluate the evaluation of memory ability by administration of *Lactobacillus paracasei*-derived vesicles in a degenerative brain disease mouse model based on the above examples, as illustrated in FIG. 6, a test was performed to confirm whether mice remembered associated fear/anxiety for a long period of time of 24, 72, and 120 hours after making the mice learn fear and anxiety associated with chamber context by applying an electric shock to the paws of the mice when the mice entered a dark chamber.

Figure 6:
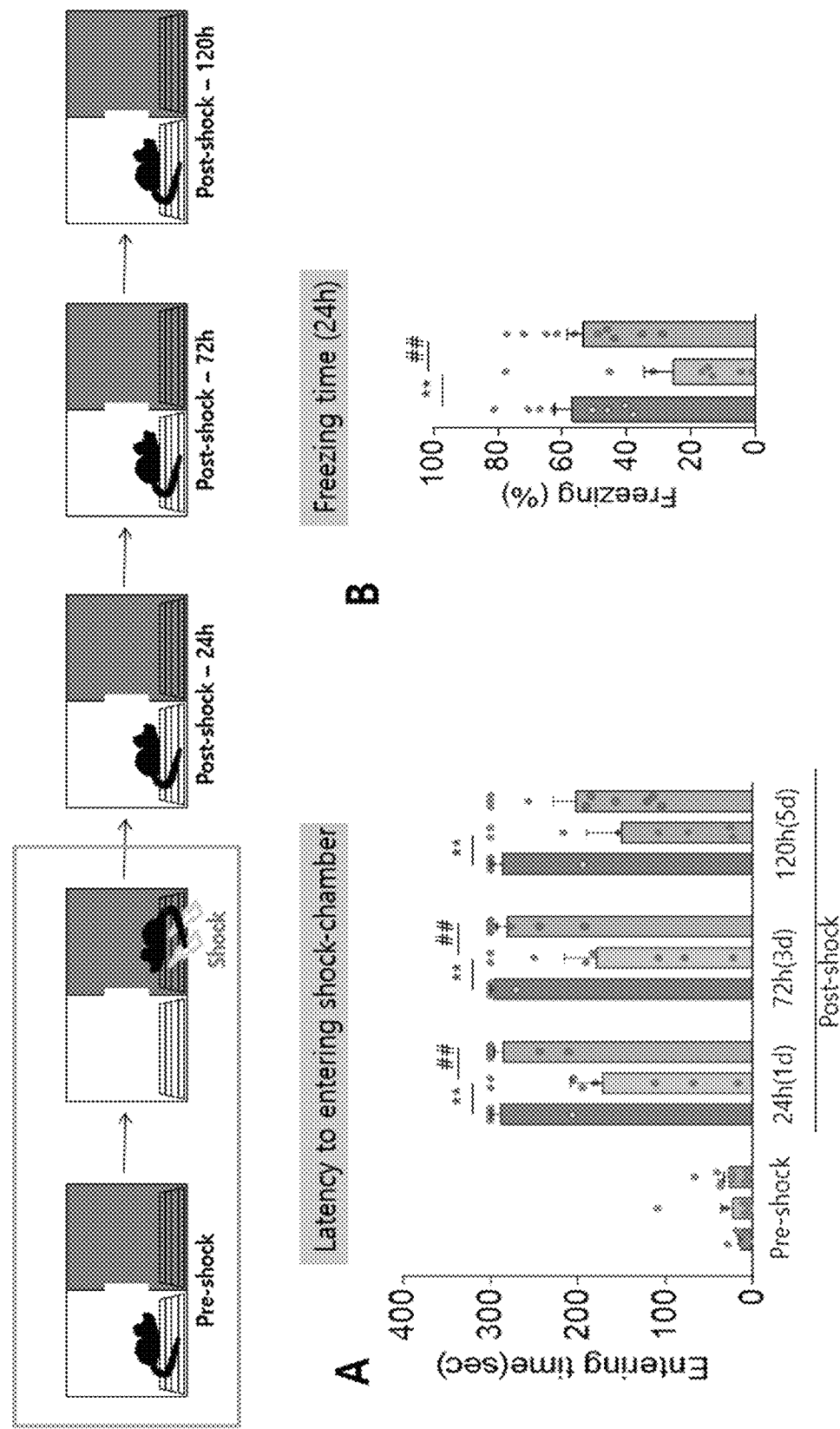
FIG. 6 illustrates the results of evaluating the memory ability efficacies in a normal mouse group (WT-CON), a degenerative brain disease mouse model (Tg-CON) group, and a group (Tg+MDH001) to which *Lactobacillus paracasei*-derived vesicles (MDH-001) are orally administered, which are a result (A) of measuring the time it takes for mice in each group, who are electrically shocked when entering a dark chamber, to enter the dark chamber, and a result (B) of measuring a freezing time that mice in each group, who have been electrically shocked, exhibit.

As a result, as illustrated in A of FIG. 6, mice of the normal mouse group (WT-CON) and mice of the degenerative brain disease mouse model group (Tg+MDH-001) to which *Lactobacillus paracasei*-derived vesicles were administered did not enter the dark chamber even after 300 seconds when the experiment passed a time point of 24, 72, and 120 hours, but the time when mice of the degenerative brain disease mouse model group (Tg-CON) entered the dark chamber gradually became faster.

Further, as illustrated in B of FIG. 6, it could be confirmed that when the mouse entered a dark chamber and came out of the dark chamber after receiving an electric shock, mice of the WT-CON and Tg+MDH-001 groups have similar high freezing time due to shock, but mice of the Tg-CON group had less freezing time than mice of the WT-CON and Tg+MDH-001 groups. The results mean that *Lactobacillus paracasei*-derived vesicles also have an effect of restoring the memory ability of mice with a degenerative brain disease.

Example 6. Evaluation of Formation of Amyloid Beta Plaques of *Lactobacillus paracasei*-Derived Vesicles in Mouse of Neurological Disorder Amyloid beta (Aβ) plaque is a protein representatively found in the brain of a patient with Alzheimer's disease, and in a Tg-APP/PS1 model, it is known that the Aβ plaque begins to accumulate in the mouse brain and induces Alzheimer's symptoms. An accumulated Aβ plaque was analyzed by fluorescently staining mouse brain sections with a Thioflavin-S dye.

Figure 7:
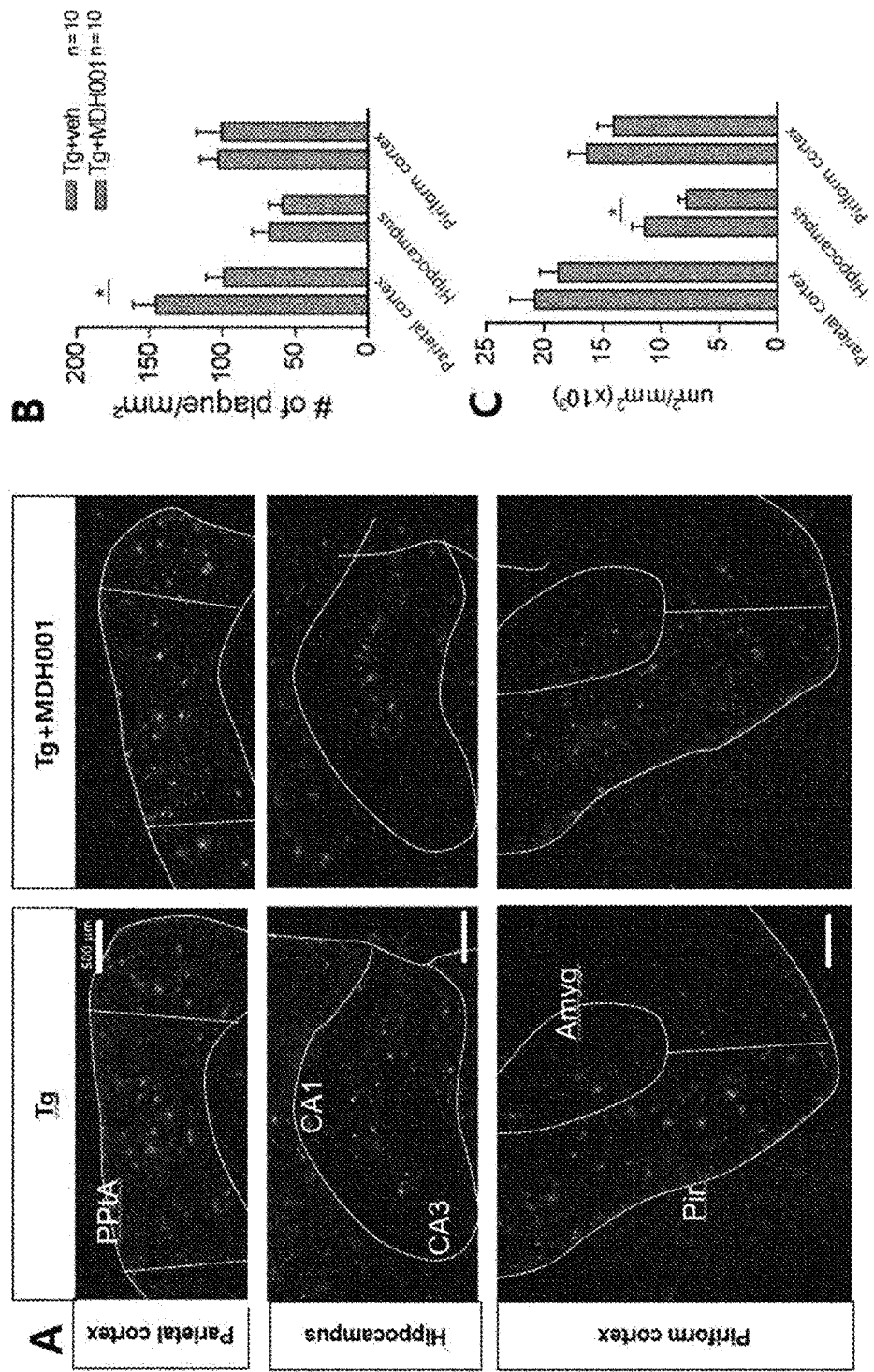
FIG. 7 illustrates the results of comparing fluorescence staining images and quantitative data of amyloid beta (Aβ) plaques in brain for each group in a degenerative brain disease animal model, which are the results illustrating a representative Aβ plaque staining photograph (A) for each group, the number (B) of Aβ plaques per unit area, and the area (C) of Aβ plaques per unit area.

As a result, as illustrated in A of FIG. 7, it could be confirmed that Aβ plaques deposited in the parietal cortex, hippocampus, and piriform cortex regions of the brain of a degenerative brain disease mouse (Tg+MDH-001) to which *Lactobacillus paracasei*-derived vesicles were administered had a difference from the degenerative brain disease mouse model group (Tg-CON).

In addition, as illustrated in B and C of FIG. 7, it was confirmed that the number of Aβ plaques and the area of Aβ plaques per unit area deposited in the parietal cortex and piriform cortex regions of the brain of the Tg+MDH-001 group decreased compared to the Tg-CON group. The above results mean that *Lactobacillus paracasei*-derived vesicles have an effect of suppressing the accumulation of the Aβ plaques in the degenerative brain disease mouse model.

Example 7. Evaluation of Nerve Cell Regeneration Ability of *Lactobacillus paracasei*-Derived Vesicles in Mouse Model of Neurological Disorder Based on the above examples, in order to elucidate a mechanism that suppresses the deterioration of nerve function shown in a degenerative brain disease mouse model to which *Lactobacillus paracasei*-derived vesicles were administered, neurogenesis was first evaluated.

Figure 8:
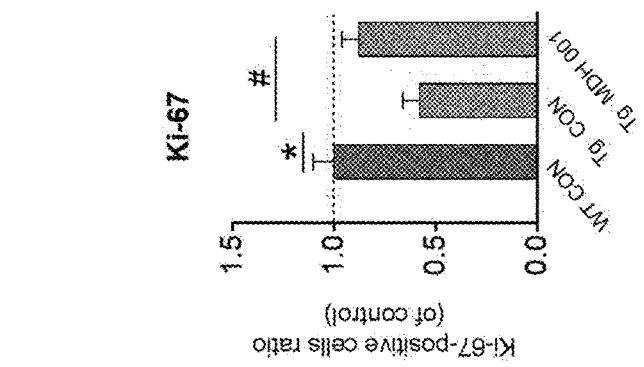
FIG. 8 illustrates the results of showing the expression of Ki-67, which is a marker for initial neurogenesis, in the brain for each group in a degenerative brain disease animal model by fluorescence staining images and quantitative data, which are representative Ki-67 staining photos (A) for each group, and a result (B) illustrating ratios of the number of cells stained with Ki-67 in a degenerative brain disease mouse model group (Tg-CON) and a group (Tg+MDH001) to which *Lactobacillus paracasei*-derived vesicles (MDH-001) are administered to that in a normal mouse group (WT-CON).
Figure 8:
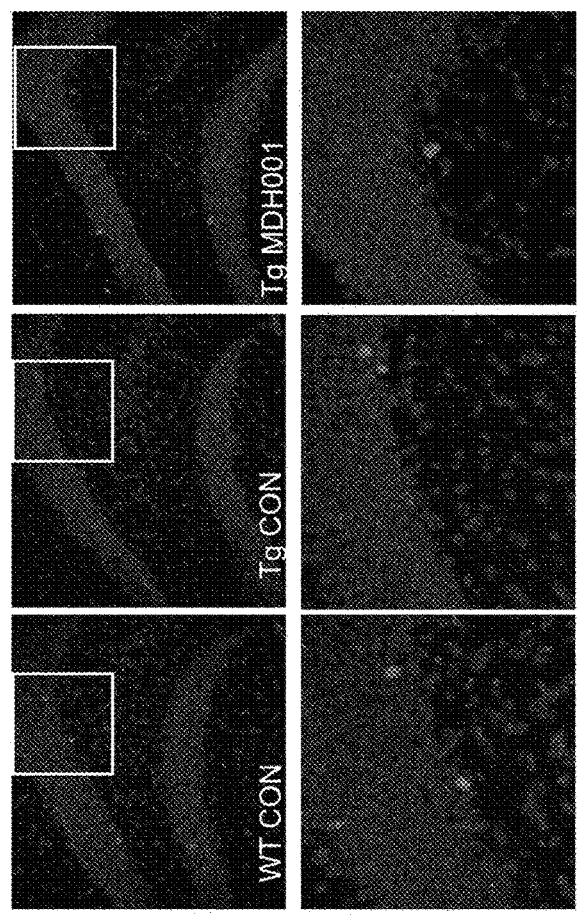

As illustrated in FIG. 8, it was observed that when the number of cells stained with Ki-67, which is known as a marker for neural differentiation, was confirmed by fluorescently staining cells with Ki-67, the number of cells stained with Ki-67 in the degenerative brain disease mouse model group (Tg-CON) decreased compared to the normal mouse group (WT-CON).

Furthermore, it was observed that the number of cells stained with Ki-67 in the group (Tg+MDH-001) to which *Lactobacillus paracasei*-derived vesicles were administered increased compared to the Tg-CON group, and it was confirmed the number was restored to the WT-CON level.

Doublecortin (DCX) expressed in neural stem cells was also analyzed as a marker for neural stem cell proliferation (neurogenesis).

Figure 9:
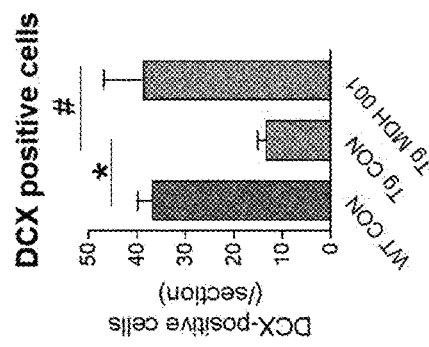
FIG. 9 illustrates the results of showing the expression of doublecortin (DCX) which is a marker for neurogenesis at metaphase or later in the brain for each group in a degenerative brain disease animal model by fluorescence staining images and quantitative data, which are representative doublecortin staining photos (A) for each group, and a result (B) illustrating the average number of cells stained with doublecortin for each section observed under a microscope in a degenerative brain disease mouse model (Tg-CON) and a group (Tg+MDH001) to which *Lactobacillus paracasei*-derived vesicles (MDH-001) are administered compared to a normal mouse group (WT-CON).
Figure 9:
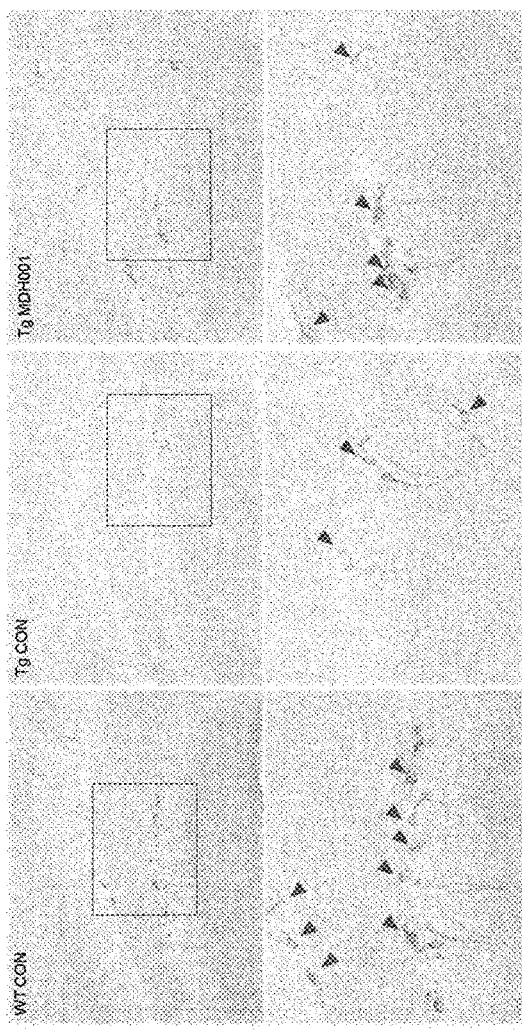

As illustrated in FIG. 9, it was observed that the number of cells stained with doublecortin in the Tg-CON group decreased compared to the WT-CON group, and it was confirmed that the number of cells stained with doublecortin in the Tg+MDH-001 group treated with *Lactobacillus paracasei*-derived vesicles increased compared to the Tg-CON group, and was restored to the WT-CON level. Through the above results, it could be seen that *Lactobacillus paracasei*-derived vesicles induced neurogenesis in a degenerative brain disease mouse model, and it was confirmed that an improvement in brain nerve function by *Lactobacillus paracasei*-derived vesicles was associated with neurogenesis of brain nerve cells.

Example 8. Evaluation of Ability of *Lactobacillus paracasei*-Derived Vesicles to Produce Nerve Cell Dendrites in Mouse Model of Neurological Disorder Based on the above examples, in order to elucidate an action mechanism for the improvement in nerve function shown in a degenerative brain disease mouse model to which *Lactobacillus paracasei*-derived vesicles were administered, the ability of nerve cells to form dendrites (dendritic process) was evaluated. Since changes in the morphology and number of dendrites may affect memory restoration, the expression of microtubule-associated protein 2 (MAP2), which is well known as a nerve marker and nerve-specific cytoskeletal protein, was confirmed. Additionally, MAP2 serves to determine the shape of dendrites during neurodevelopment, stabilize growth, and stabilize the growth of microtubules.

Figure 10:
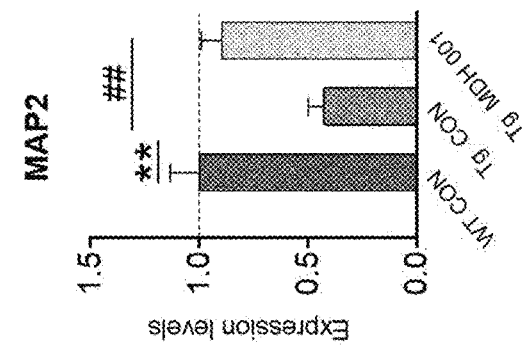
FIG. 10 illustrates the results of showing the expression of microtubule-associated protein 2 (MAP2), which is a neuron-specific cytoskeletal protein in the brain, for each group in a degenerative brain disease animal model by fluorescence staining images and quantitative data, which are representative MAP2 staining photos (A) for each group, and a result (B) illustrating ratios of the expression of MAP2 in a degenerative brain disease mouse model group (Tg-CON) and a group (Tg+MDH001) to which *Lactobacillus paracasei*-derived vesicles (MDH-001) are administered to that in a normal mouse group (WT-CON).
Figure 10:
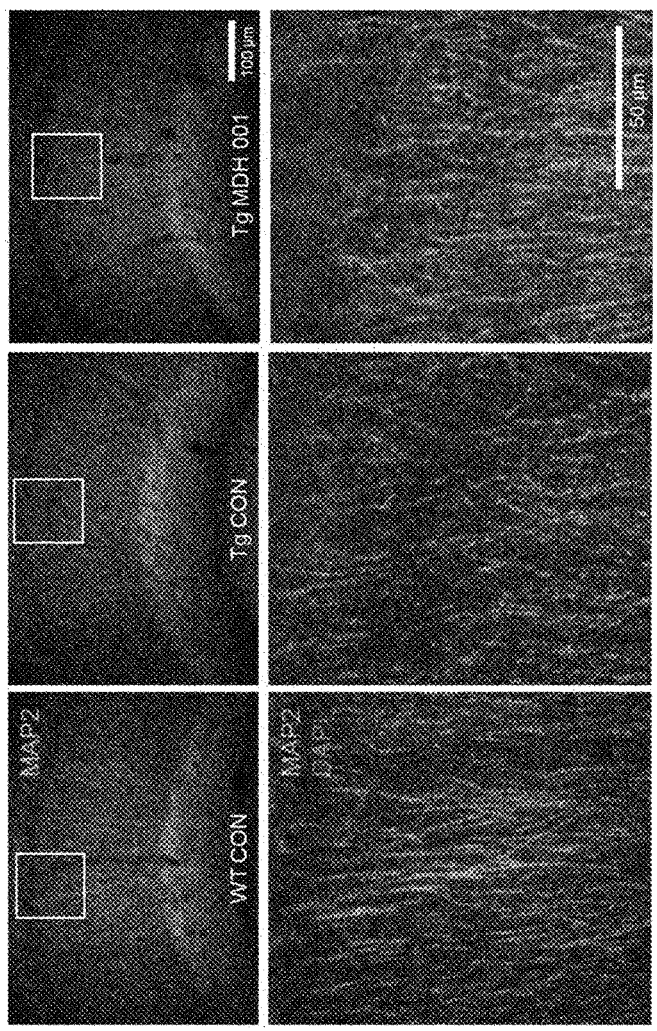

As a result, as illustrated in FIG. 10, it was observed that the expression of MAP2 in the degenerative brain disease mouse model group (Tg-CON) decreased compared to the normal mouse group (WT-CON). It was confirmed that the expression of MAP2 in the group (Tg+MDH001) in which *Lactobacillus paracasei*-derived vesicles were administered to the degenerative brain disease mouse model was increased compared to the Tg-CON group, and restored to the WT-CON level. Through the result, it could be seen that *Lactobacillus paracasei*-derived vesicles had an effect of restoring MAP2 in the degenerative brain disease mouse model, and *Lactobacillus paracasei*-derived vesicles improved neural function by protecting the microstructure of dendrites to improve intercellular integrity.

Figure 11:
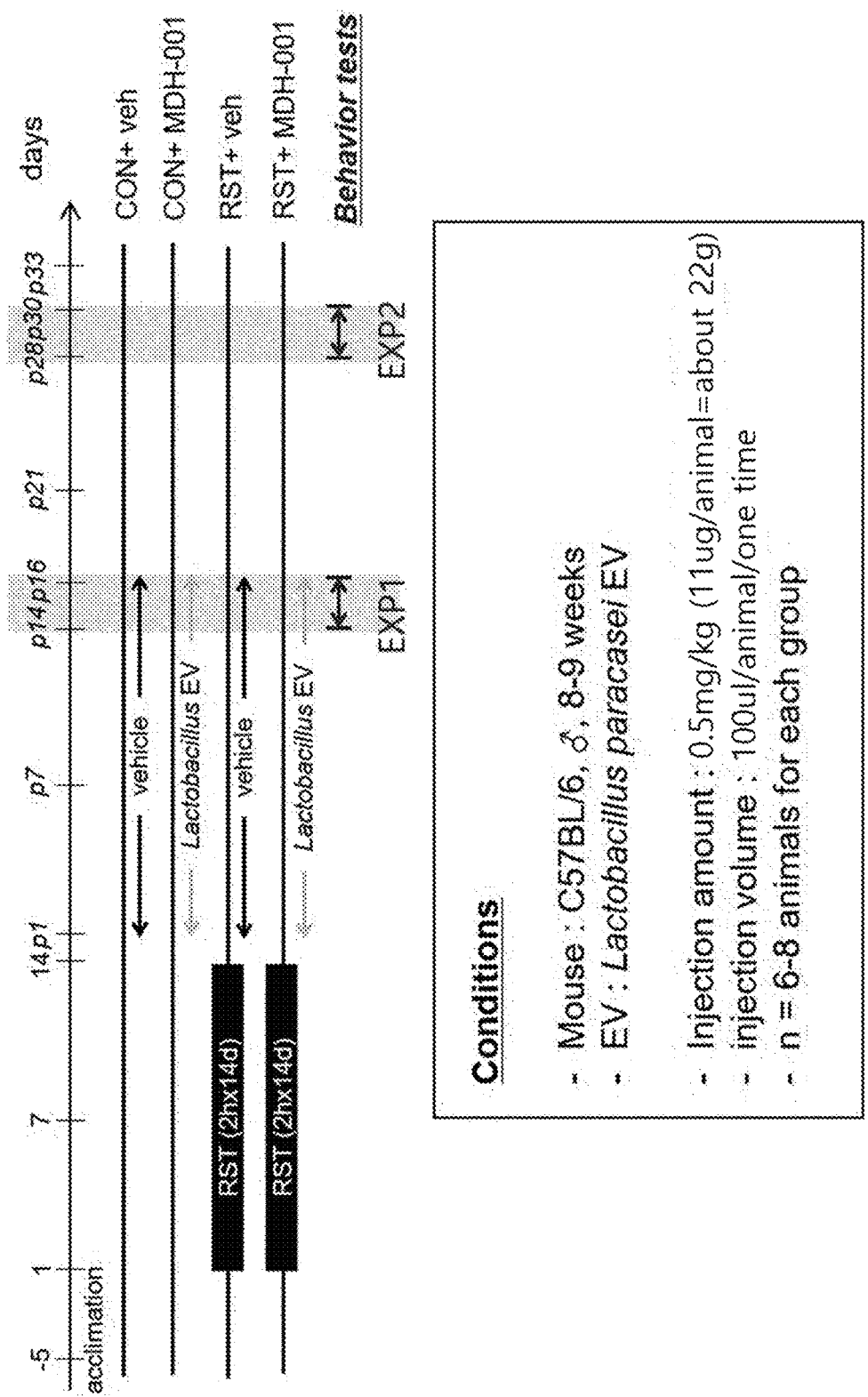
FIG. 11 is a view illustrating an experimental protocol for evaluating the therapeutic effect of *Lactobacillus paracasei*-derived vesicles (EVs) on mental function in an animal model of mental disorder induced by mental stress [CON or CON+Veh: saline-administered normal mouse group (control, saline-administered control), CON+MDH-001: *Lactobacillus paracasei* vesicles-administered normal mouse group, RST+Veh: saline-administered stress treatment group, RST+MDH-001: *Lactobacillus paracasei* vesicles-administered stress treatment group].

Example 9. Therapeutic Effect of *Lactobacillus paracasei*-Derived Vesicles on Mental Function on Day 14 to 16 After Mental Stress Stimulation in Mouse Model of Mental Disorder Through an experiment using mice, it was intended to investigate whether behavioral induction due to changes in emotional function due to stress was blocked when *Lactobacillus paracasei*-derived vesicles were administered after mental stress stimulation. For this purpose, according to the experimental process illustrated in FIG. 11, an experiment was performed by purchasing 7-week-old male C57BL/6 mice and randomly dividing the mice into four groups, that is, a normal mouse group (CON or CON+Veh) to which saline (0.9% saline, 100 μl) was administered for 14 days, a normal mouse group (CON+MDH-001) to which *Lactobacillus paracasei*-derived vesicles (2 μg/mouse/100 μl) were administered, a group (RST+Veh) in which saline (0.9% saline, 100 μl) was administered to mice subjected to physical restraint stress (RST) 2 hours daily for 14 days, and a group (RST+MDH-001) in which *Lactobacillus paracasei*-derived vesicles (EV, 2 μg/mouse/100 μl) were administered to mice subjected to physical restraint stress 2 hours daily for 14 days. The experiment was performed in the order of a U-BOX test to measure sociability, a tail suspension test (TST), and a forced swimming test (FST), and the therapeutic effect on depression caused by administration of extracellular vesicles on day 14 to 16 after stress stimulation was evaluated.

First, the U-BOX test was performed on mice of the four groups described above that were subjected to the experiments. As illustrated in A of FIG. 12, in the test, it was confirmed how much time contact was made with a target mouse by placing the target mouse in a wire mesh on one side of a U-shaped field, and placing only a wire mesh on the opposite side without the target mouse.

Figure 12:
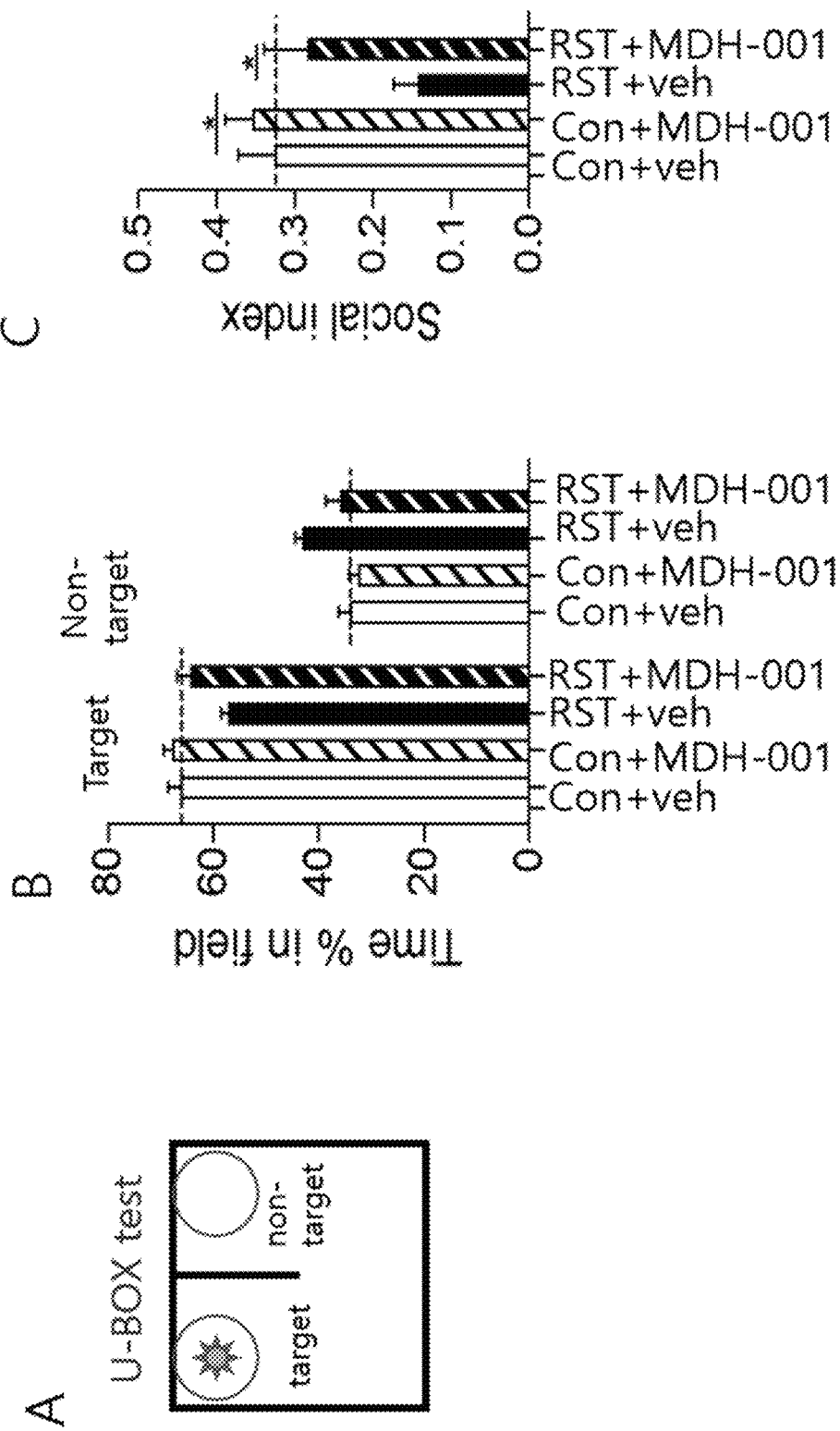
FIG. 12 illustrates the results of evaluating a social test protocol (A) and social indices (B and C) for each mouse group in order to evaluate the therapeutic effects of *Lactobacillus paracasei*-derived vesicles on emotional function on day 14 to 16 after stressing an animal model of mental disorder induced by mental stress.

As a result, as illustrated in B of FIG. 12, it was shown that in a control (CON+Veh) and a group (CON+MDH-001) in which vesicles were administered to the control, the time the mice spent in a target space (Target) was increased compared to the time the mice spent in a non-target space, but in the case of the group (RST+Veh) in which the mice were subjected to physical restraint stress, the mice spent less time in the target space than the other groups.

In contrast, as illustrated in C of FIG. 12, it was confirmed that in the group (RST+MDH-001) to which vesicles were together administered, the time spent with the target mouse was increased to a level similar to that of the control.

Figure 13:
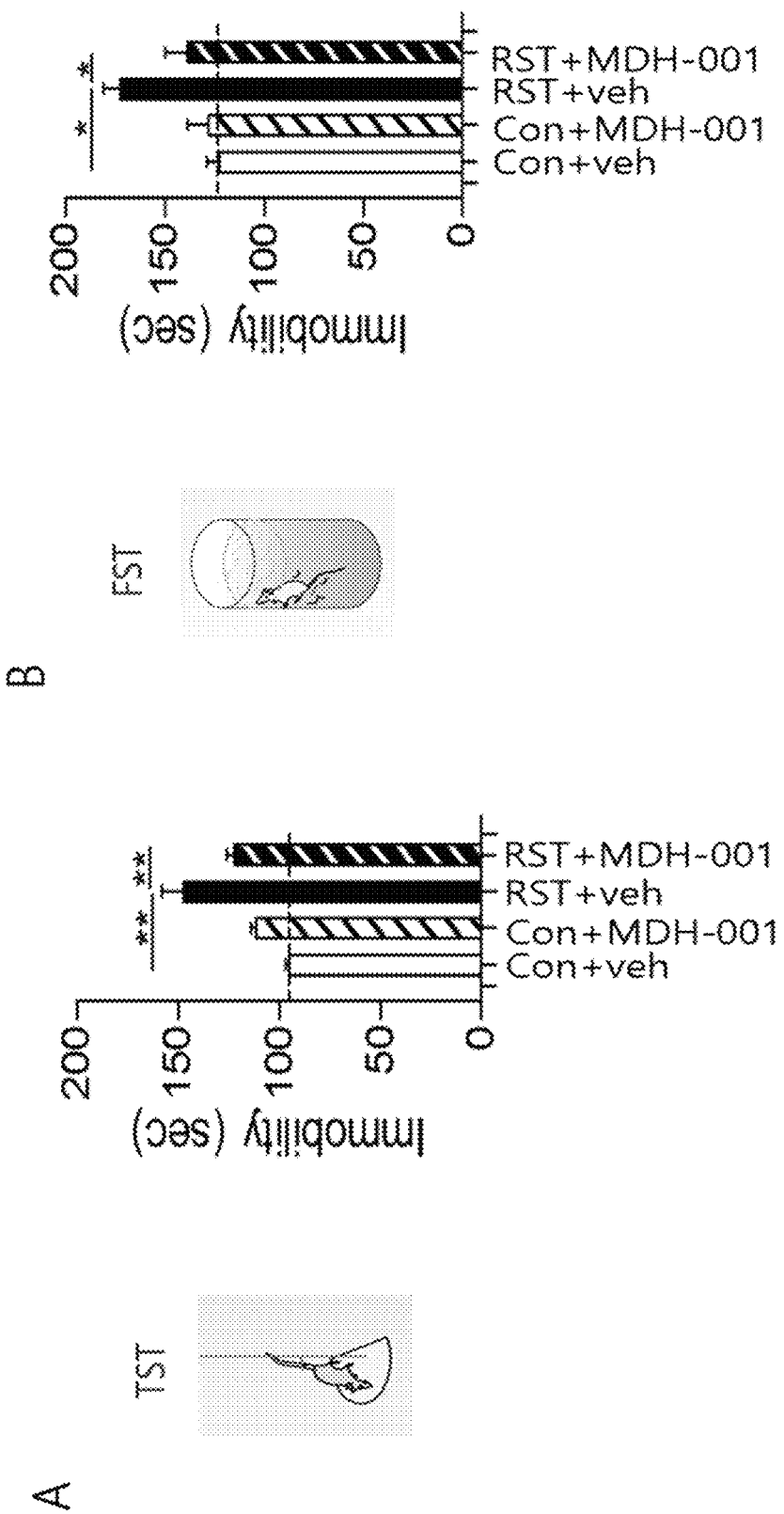
FIG. 13 illustrates the results of performing a tail suspension test (TST) (A) and a forced swim test (FST) (B), respectively, on each mouse group in order to evaluate the therapeutic effects of *Lactobacillus paracasei*-derived vesicles on emotional function on day 14 to 16 after stressing an animal model of mental disorder induced by mental stress.

Further, as illustrated in FIG. 13, it was confirmed that as a result of performing a tail suspension test (TST) and a forced swim test (FST), respectively, the immobility in the group (RST+Veh) subjected to physical restraint stress was increased compared to the control (CON+Veh), whereas in the case of the group (RST+MDH-001) to which vesicles were administered, the immobility was decreased.

Example 10. Therapeutic Effect of *Lactobacillus paracasei*-Derived Vesicles on Mental Function on Day 28 to 30 After Mental Stress Stimulation in Mouse Model of Mental Disorder After an experiment was performed in the same manner as in Example 9, the therapeutic effect of *Lactobacillus paracasei*-derived vesicles on day 28 to 30 after stress stimulation on an emotional disorder was evaluated.

Figure 14:
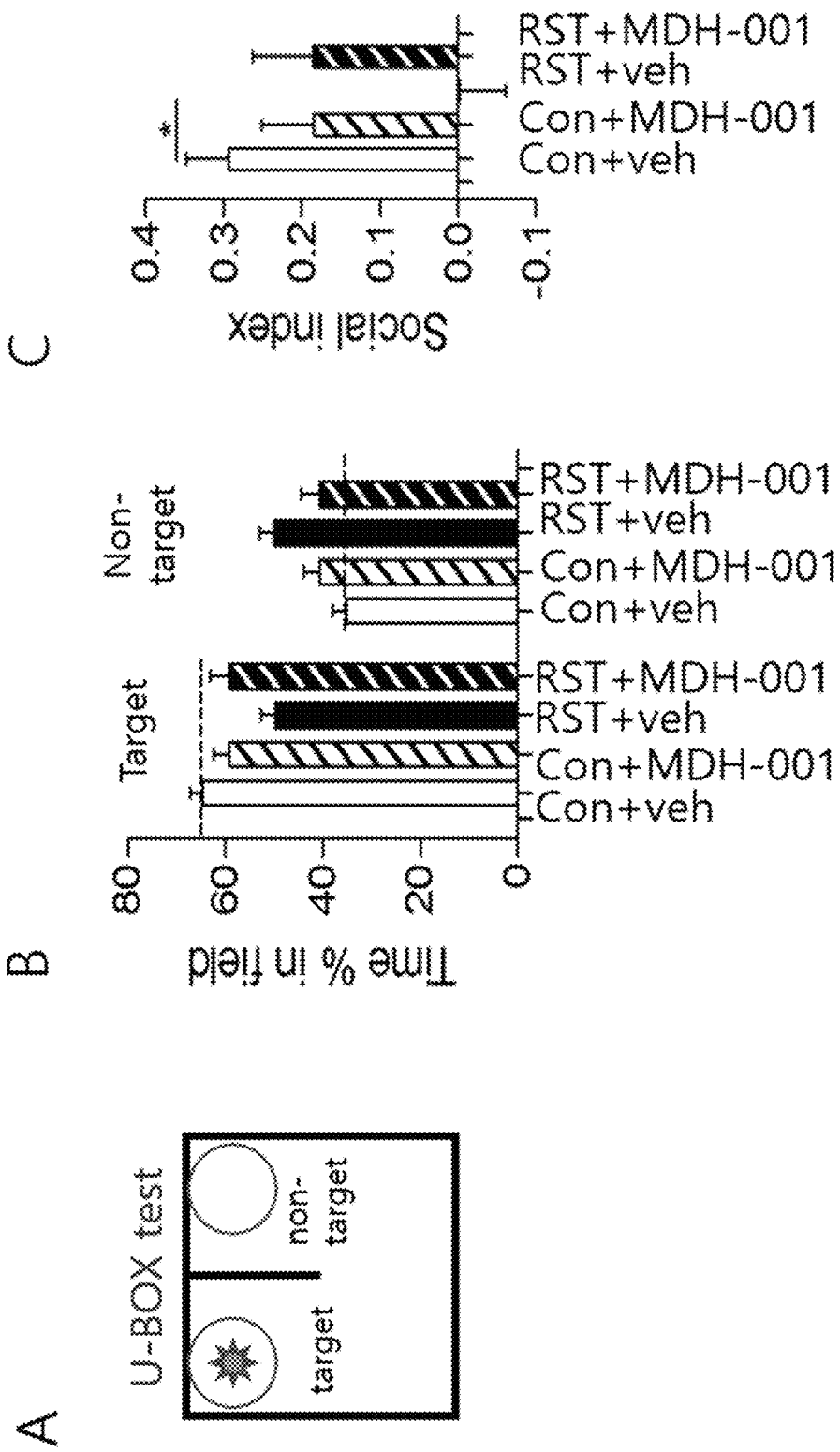
FIG. 14 illustrates the results of evaluating a social test protocol (A) and social indices (B and C) for each mouse group in order to evaluate the therapeutic effects of *Lactobacillus paracasei*-derived vesicles on depression on day 28 to 30 after stressing an animal model of mental disorder induced by mental stress.

First, as a result of the U-BOX test, as illustrated in FIG. 14, under the target conditions, the time a stressed control (RST+Veh) spent in the target space (Target) decreased compared to the control (CON+Veh). In contrast, it was confirmed that in a stressed and extracellular vesicles-administered group (RST+MDH-001), the time the mice spent in the target space was restored to the level of the control.

Figure 15:
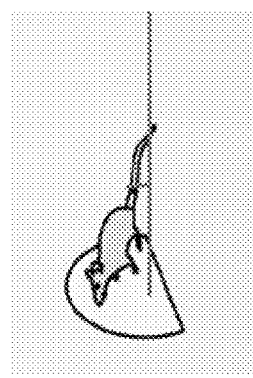
FIG. 15 illustrates the results of performing a tail suspension test (TST) on each mouse group in order to evaluate the therapeutic effects of *Lactobacillus paracasei*-derived vesicles on depression on day 28 to 30 after stressing an animal model of mental disorder induced by mental stress.
Figure 15:
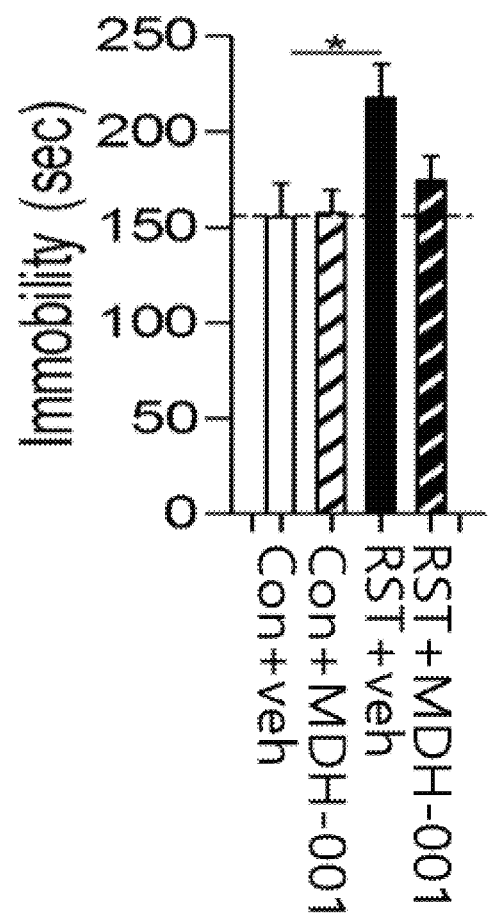

Next, as a result of performing a tail suspension test, respectively, as illustrated in FIG. 15, it was confirmed that in the stressed group (RST+Veh), the immobility was significantly increased compared to the control (CON+Veh), whereas in the stressed and vesicles-administered group (RST+MDH-001), the immobility time was decreased to the level of the control.

Through the results of Examples 9 and 10, it could be seen that when *Lactobacillus paracasei*-derived vesicles were administered to mice after mental stress, *Lactobacillus paracasei*-derived vesicles effectively suppressed the impairment of mental function that occurs after stress.

Example 11. Evaluation of Effects of *Lactobacillus paracasei*-Derived Vesicles on Activation of AMPK in Cells Cultured In Vitro Cellular senescence is defined as the loss of cell division ability due to repeated physical, chemical, biological, and mental stress, and repeated stress causes cell regeneration ability to deteriorate along with senescence of cells, resulting in senescence-related diseases. Recently, activation of AMPK protein has attracted attention as an intracellular signaling pathway that suppresses cellular senescence. Based on this background, in the present example, an experiment was performed by the following method to evaluate the effect of *Lactobacillus paracasei*-derived vesicles (MDH-001) on cellular senescence through intracellular AMPK activation.

In order to evaluate the activity of AMPK according to the concentration of *Lactobacillus paracasei*-derived vesicles treated in vitro, cells were treated with *Lactobacillus paracasei*-derived vesicles at a concentration of 0, 0.1, 1, and 10 μg/ml for 1 hour. Insulin, which promotes senescence, and metformin, which suppresses senescence, were used as controls. After cells were treated with the drugs, the difference in the amount of pAMPK, which is an important index in AMPK signaling, was measured by western blotting.

Figure 16:
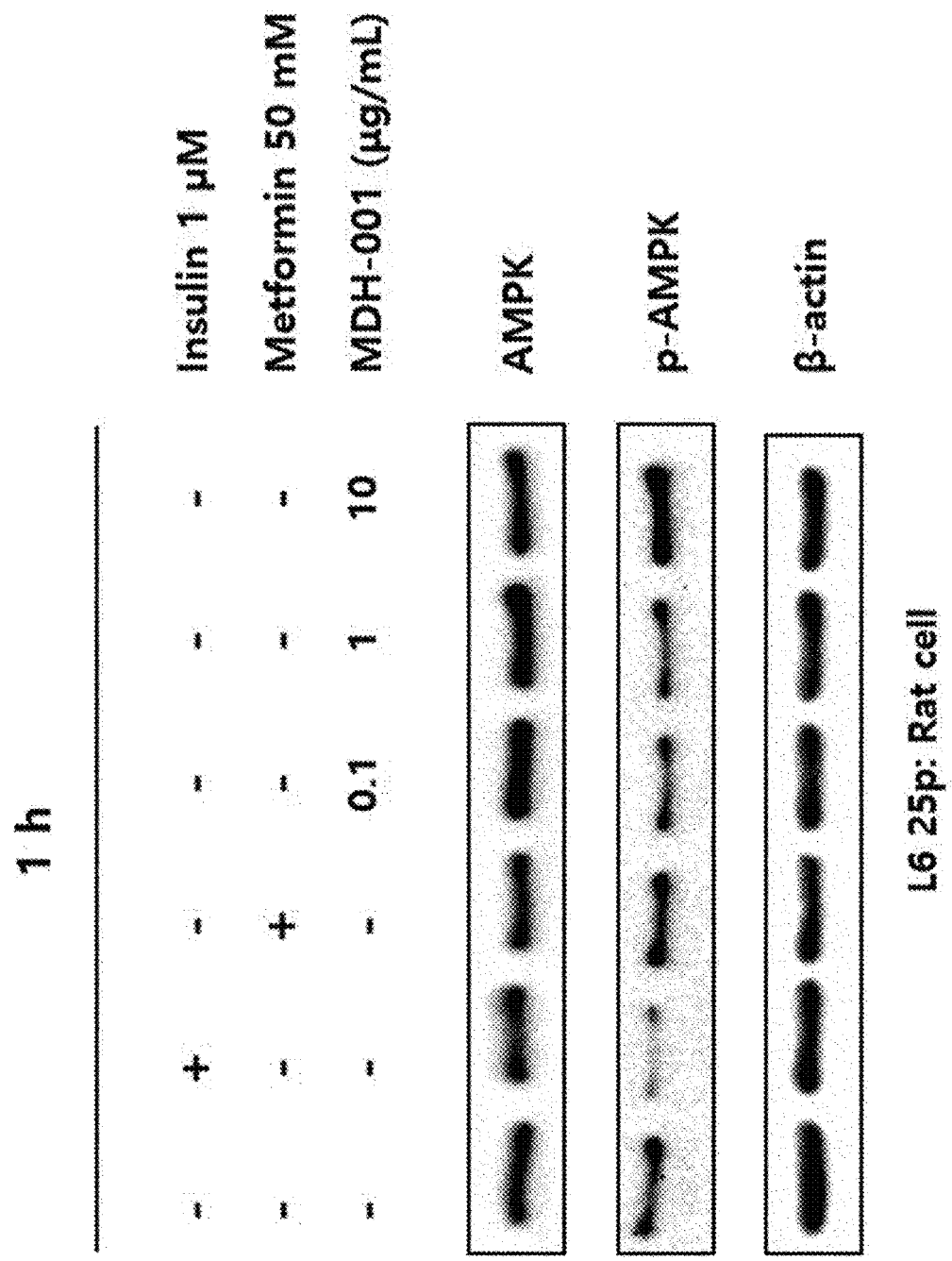
FIG. 16 illustrates the results of evaluating the activation of AMPK at 60 minutes after administering insulin that promotes senescence in cells ex vivo, metformin which is a control drug that suppresses senescence, and *Lactobacillus paracasei*-derived vesicles (MDH-00) at various concentrations in order to evaluate a therapeutic action mechanism for cellular senescence by various stresses.

As a result, as illustrated in FIG. 16, the expression of pAMPK was increased by metformin, which is a positive control, and even when cells were also treated with *Lactobacillus paracasei*-derived vesicles, the expression of pAMPK was increased in an vesicle concentration-dependent manner.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The present inventors confirmed that vesicles derived from *Lactobacillus paracasei* was delivered to the brain when orally administered, and confirmed that when vesicles derived from *Lactobacillus paracasei* were orally administered to a degenerative neurological disorder model, learning ability and memory were improved to normal levels, the deposition of amyloid plaques in brain tissues was suppressed, the proliferation of stem cells in the hippocampus was improved to normal levels, and the formation of nerve cell dendrites was restored to normal levels. Thus, the present invention can be used as a composition for preventing, improving, or treating a neurological disorder or mental disorder, comprising vesicles derived from *Lactobacillus paracasei* as an active ingredient, and thus has industrial applicability.

The invention claimed is:

1. A method for improving cognitive function or reducing accumulated Amyloid beta (Aβ) plaque in a subject with a neurological disorder comprising administering to the subject a composition comprising *Lactobacillus paracasei*-derived extracellular vesicles as an active ingredient, and thereby improving the cognitive function or reducing the accumulated Aβ plaque, wherein the vesicles are isolated from a *Lactobacillus paracasei* culture solution.

2. The method of claim 1, wherein the neurological disorder is selected from the group consisting of autism spectrum disorder, mild cognitive impairment, dementia, Alzheimer's disease, Parkinson's disease, Huntington's disease, amyotrophic lateral sclerosis (ALS), Batten disease, Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), mitochondrial recessive ataxia syndrome, and a combination of thereof.

3. The method of claim 1, wherein the vesicles have an average diameter of 10 to 1000 nm.

4. The method of claim 1, wherein the vesicles are naturally or artificially secreted from *Lactobacillus paracasei*.

5. The method of claim 1, wherein the composition is a pharmaceutical composition.

6. The method of claim 1, wherein the composition is a food composition.

7. The method of claim 1, wherein the composition is an inhalation composition.

8. The method of claim 1, wherein the improvement is by suppression of progression of short-term and long-term cognitive impairments, restoration of spatial perceptual learning or memory, restoration of memory ability, suppression of accumulated Aβ plaque, induction of neurogenesis, or protection of microstructure of dendrites to improve intercellular integrity.

* * * * *